United States Patent
Dong et al.

(10) Patent No.: US 9,314,509 B2
(45) Date of Patent: Apr. 19, 2016

(54) PHARMACEUTICAL COMPOSITIONS OF MELANOCORTIN RECEPTOR LIGANDS

(75) Inventors: Zheng Xin Dong, Holliston, MA (US); Jundong Zhang, Newton, MA (US)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

(21) Appl. No.: 13/508,777

(22) PCT Filed: Nov. 15, 2010

(86) PCT No.: PCT/US2010/056690
§ 371 (c)(1),
(2), (4) Date: May 9, 2012

(87) PCT Pub. No.: WO2011/060352
PCT Pub. Date: May 19, 2011

(65) Prior Publication Data
US 2012/0225816 A1    Sep. 6, 2012

Related U.S. Application Data

(60) Provisional application No. 61/281,360, filed on Nov. 16, 2009.

(51) Int. Cl.
| | |
|---|---|
| *A61K 38/12* | (2006.01) |
| *A61P 5/00* | (2006.01) |
| *A61K 38/33* | (2006.01) |
| *A61K 9/00* | (2006.01) |
| *A61K 9/08* | (2006.01) |
| *A61K 38/34* | (2006.01) |
| *C07K 14/68* | (2006.01) |
| *C07K 14/69* | (2006.01) |

(52) U.S. Cl.
CPC ............... *A61K 38/33* (2013.01); *A61K 9/0019* (2013.01); *A61K 9/08* (2013.01); *A61K 38/34* (2013.01); *C07K 14/68* (2013.01); *C07K 14/69* (2013.01); *A61K 9/0024* (2013.01)

(58) Field of Classification Search
CPC ..... A61K 38/33; A61K 38/34; A61K 9/0019; A61K 9/0024; A61K 9/08; C07K 14/68; C07K 14/69
See application file for complete search history.

(56) References Cited

U.S. PATENT DOCUMENTS

| | | | |
|---|---|---|---|
| 6,768,024 B1 * | 7/2004 | Watson-Straughan et al. ........................... | 564/367 |
| 2005/0159356 A1 | 7/2005 | Dong et al. | |
| 2006/0039862 A1 | 2/2006 | Andersen et al. | |
| 2008/0171700 A1 | 7/2008 | Nilsson et al. | |
| 2008/0207493 A1 * | 8/2008 | Pettersson et al. .................. | 514/9 |
| 2008/0306008 A1 | 12/2008 | Sensfuss et al. | |
| 2013/0210751 A1 | 8/2013 | Dong et al. | |

FOREIGN PATENT DOCUMENTS

| | | | | |
|---|---|---|---|---|
| WO | 94/06452 A1 | 3/1994 | | |
| WO | 95/15767 A1 | 6/1995 | | |
| WO | 99/44642 A1 | 9/1999 | | |
| WO | WO 0071163 A1 * | 11/2000 | ............. | A61K 47/22 |
| WO | 01/03723 A1 | 1/2001 | | |
| WO | 02/17918 A2 | 3/2002 | | |
| WO | 2005102377 A1 | 11/2005 | | |
| WO | 2005120453 A1 | 12/2005 | | |
| WO | 2007/008704 | 1/2007 | | |
| WO | 2007/084460 A2 | 7/2007 | | |
| WO | 2008/041245 A2 | 4/2008 | | |
| WO | 2009061411 A2 | 5/2009 | | |
| WO | WO 2009139855 A2 * | 11/2009 | ............. | A61K 38/12 |
| WO | 2010/016936 A1 | 2/2010 | | |
| WO | 2010/018159 A1 | 2/2010 | | |
| WO | 2011/117851 A1 | 9/2011 | | |

OTHER PUBLICATIONS

Meredith Mason-Garcia, Radioimmunoassay for octapeptide analogs of somatostatin: Measurement of serum levels after administration of long-acting microcapsule formulations, Proc. Natl. Acad. Sci. USA, vol. 85, pp. 5688-5692, Aug. 1988.*

Anushree Datta, Characterization of Polyethylene Glycol Hydrogels for Biomedical Applications,University of Pune, India, Thesis (Aug. 2007).*

Aleksandrovich, L. N. et al., "Pharmaceutical Formulation of Anti-Inflammatory and Antibacterial Action in Ointment Form with Hydrophobic Base Applied for Dermatoses Treatment", RU Patent Publication No. 2 325 912 C1, Abstract only.

Zhulenko, V. V., Pharmacology, Moscow, KolosS, 2008 (publisher), p. 21.

(Continued)

*Primary Examiner* — James H Alstrum Acevedo
*Assistant Examiner* — Erinne Dabkowski
(74) *Attorney, Agent, or Firm* — Eileen J. Ennis; Janice M. Klunder (57) ABSTRACT

The present invention relates to improvements in compositions containing peptides that are ligands of one or more of the melanocortin receptors (MC-R), or pharmaceutically acceptable salts thereof, methods for preparing such compositions, and method of using such compositions to treat mammals. In particular, the present invention relates to a pharmaceutical composition comprising a pamoate salt of Ac-Arg-cyclo (Cys-D-Ala-His-D-Phe-Arg-Trp-Cys)-NH$_2$ which is a ligand of the melanocortin receptor subtype 4 (MC4-R), and in which, after subcutaneous or intramuscular administration to a subject, the peptide forms a depot at physiological pH that is slowly dissolved and released into the body fluid and bloodstream. The present invention may further comprise an organic component such as dimethylacetamide (DMA) or polyethylene glycol (PEG) with an average molecular weight of lower than 1000.

10 Claims, 7 Drawing Sheets

(56) References Cited

OTHER PUBLICATIONS

Volchek, I.A., et al., "Pharmaceutical Composition with Cytokine and Immunomodulating Effects", RU Patent Publication No. 2 222 345 C2, Abstract only.

Translation of Second Office Action for related Chinese Application No. 201080051808.2.

Henning, Torsten, Polyethylene glycols (PEGs) and the pharmaceutical industry, Fine, Speciality & Performance Chemicals, Jun. 2002, pp. 57-59.

Packhaeuser, C.B. et al., In situ forming parenteral drug delivery systems: an overview, EP J. of Pharmaceuticals and Biopharmaceutics, Apr. 2004, pp. 445-455, vol. 58.

* cited by examiner

PHARMACEUTICAL COMPOSITIONS OF MELANOCORTIN RECEPTOR LIGANDS

This application is a United States nation stage filing under 35U.S.C. §371of international (PCT) application no. PCT/US10/056690 filed Nov.15 2010, and designating the U.S, which claims priority to U.S. provisional application No. 61/281360 filed Nov. 16 2009.

BACKGROUND OF THE INVENTION

The present invention relates to improvements in compositions containing peptides that are ligands of one or more of the melanocortin receptors (MC-R), or pharmaceutically acceptable salts thereof, methods for preparing such compositions, and method of using such compositions to treat mammals. In particular, the present invention relates to a pharmaceutical composition comprising a pamoate salt of Ac-Arg-cyclo(Cys-D-Ala-His-D-Phe-Arg-Trp-Cys)-NH$_2$ which is a ligand of the melanocortin receptor subtype 4 (MC4-R), and in which, after subcutaneous or intramuscular administration to a subject, the peptide forms a depot at physiological pH that is slowly dissolved and released into the body fluid and bloodstream. The present invention may further comprise an organic component such as dimethylacetamide (DMA) or polyethylene glycol (PEG) with an average molecular weight of lower than 1000.

Melanocortins are a family of regulatory peptides which are formed by post-translational processing of pro-hormone pro-opiomelanocortin (POMC; 131 amino acids in length). POMC is processed into three classes of hormones; the melanocortins, adrenocorticotropin hormone, and various endorphins (e.g. lipotropin) (Cone, et al., Recent Prog. Horm. Res., 51:287-317, (1996); Cone et al., Ann. N.Y. Acad. Sci., 31:342-363, (1993)).

Melanocortins have been found in a wide variety of normal human tissues including the brain, adrenal, skin, testis, spleen, kidney, ovary, lung, thyroid, liver, colon, small intestine and pancreas (Tatro, J. B. et al., Endocrinol. 121:1900-1907 (1987); Mountjoy, K. G. et al., Science 257:1248-1251 (1992); Chhajlani, V. et al., FEBS Lett. 309:417-420 (1992); Gantz, I. et al. J. Biol. Chem. 268:8246-8250 (1993) and Gantz, I. et al., J. Biol. Chem. 268:15174-15179 (1993)).

Melanocortin peptides have been shown to exhibit a wide variety of physiological activities including the control of behavior and memory, affecting neurotrophic and antipyretic properties, as well as affecting the modulation of the immune system. Aside from their well known effects on adrenal cortical functions (adrenocorticotropic hormone or "ACTH") and on melanocytes (melanocyte stimulating hormone or "MSH"), melanocortins have also been shown to control the cardiovascular system, analgesia, thermoregulation and the release of other neurohumoral agents including prolactin, luteinizing hormone and biogenic amines (De Wied, D. et al., Methods Achiev. Exp. Pathol. 15:167-199 (1991); De Wied, D. et al., Physiol. Rev. 62:977-1059 (1982); Guber, K. A. et al., Am. J. Physiol. 257:R681-R694 (1989); Walker J. M. et al., Science 210:1247-1249 (1980); Murphy, M. T. et al., Science 221:192-193 (1983); Ellerkmann, E. et al., Endocrinol. 130:133-138 (1992) and Versteeg, D. H. G. et al., Life Sci. 38:835-840 (1986)).

It has also been shown that binding sites for melanocortins are distributed in many different tissue types including lachrymal and submandibular glands, pancreas, adipose, bladder, duodenum, spleen, brain and gonadal tissues as well as malignant melanoma tumors. Five melanocortin receptors have been characterized to date. These include melanocyte-specific receptor (MC1-R), corticoadrenal-specific ACTH receptor (MC2-R), melacortin-3 (MC3-R), melanocortin-4 (MC4-R) and melanocortin-5 receptor (MC5-R). All of the melanocortin receptors respond to the peptide hormone class of melanocyte stimulating hormones (MSH) (Cone, R. D. et al., Ann. N.Y. Acad. Sci., 680:342-363 (1993); Cone, R. D. et al., Recent Prog. Horm. Res., 51:287-318 (1996)).

MC1-R, known in the art as Melanocyte Stimulating Hormone Receptor (MSH-R), Melanotropin Receptor or Melanocortin-1 Receptor, is a 315 amino acid transmembrane protein belonging to the family of G-Protein coupled receptors. MC1-R is a receptor for both MSH and ACTH. The activity of MC1-R is mediated by G-proteins which activate adenylate cyclase. MC1-R receptors are found in melanocytes and corticoadrenal tissue as well as various other tissues such as adrenal gland, leukocytes, lung, lymph node, ovary, testis, pituitary, placenta, spleen and uterus. MC2-R, also called Adrenocorticotropic Hormone Receptor (ACTH-R), is a 297 amino acid transmembrane protein found in melanocytes and the corticoadrenal tissue. MC2-R mediates the corticotrophic effect of ACTH. In humans, MC3-R is a 360 AA protein found in brain tissue; in mice and rats MC3-R is a 323 AA protein. MC4-R is a 332 amino acid transmembrane protein which is also expressed in brain as well as placental and gut tissues. MC5-R is a 325 amino acid transmembrane protein expressed in the adrenals, stomach, lung and spleen and very low levels in the brain. MC5-R is also expressed in the three layers of adrenal cortex, predominantly in the aldosterone-producing zona glomerulosa cells.

The five known melanocortin receptors differ, however, in their functions. For example, MC1-R is a G-protein coupled receptor that regulates pigmentation in response to α-MSH, a potent agonist of MC1-R. Agonism of the MC1-R receptor results in stimulation of the melanocytes which causes eumelanin and increases the risk for cancer of the skin. Agonism of MC1-R can also have neurological effects. Stimulation of MC2-R activity can result in carcinoma of adrenal tissue. Recent pharmacological confirmation has established that central MC4-R receptors are the prime mediators of the anorexic and orexigenic effects reported for melanocortin agonists and antagonists, respectively. The effects of agonism of the MC3-R and MC5-R are not yet known.

There has been great interest in melanocortin (MC-R) receptors as targets for the design of novel therapeutics to treat disorders of body weight such as obesity and cachexia. Both genetic and pharmacological evidence points toward central MC4-R receptors as the principal target (Giraudo, S. Q. et al., Brain Res., 809:302-306 (1998); Farooqi, I. S. et al., NE J Med., 348:1085-1095 (2003); MacNeil, D. J. et al., Eu. J. Pharm., 44:141-157 (2002); MacNeil, D. J. et al., Eu. J. Pharm., 450:93-109 (2002); Kask, A. et al., NeuroReport, 10:707-711 (1999)). The current progress with receptor-selective agonists and antagonists evidences the therapeutic potential of melanocortin receptor activation, particularly MC4-R.

Agonist, antagonist or other ligand compounds activating one or more melanocortin receptor would be useful for treating a wide variety of indications in a subject in need thereof or at risk thereof including acute and chronic inflammatory diseases such as general inflammation (U.S. Pat. No. 6,613,874; Catania, A. et al., Pharm. Rev., 56:1-29 (2004)), inflammatory bowel disease (U.S. Pat. No. 6,713,487; Catania, A. et al., Pharm. Rev., 56:1-29 (2004)), brain inflammation (Catania, A. et al., Pharm. Rev., 56:1-29 (2004)), sepsis (U.S. Pat. Nos. 6,613,874; 6,713,487; Catania, A. et al., Pharm. Rev., 56:1-29 (2004)) and septic shock (U.S. Pat. No. 6,613,874; Catania, A. et al., Pharm. Rev., 56:1-29 (2004)); diseases with an autoimmune component such as rheumatoid arthritis (U.S. Pat. No. 6,713,487; Catania, A. et al., Pharm. Rev., 56:1-29 (2004)), gouty arthritis (Catania, A. et al., Pharm. Rev., 56:1-29 (2004), Getting, S. J. et al., Curr. Opin. Investig. Drugs, 2:1064-1069 (2001)), and multiple sclerosis ((U.S. Pat. No. 6,713,487); metabolic diseases and medical conditions accompanied by weight gain such as obesity (U.S. Pat. Nos. 6,613,874; 6,600,015; Fehm, H. L. et al., J. Clin. Endo. 2 Metab., 86:1144-1148 (2001); Hansen, M. J. et al., Brain Res., 1039:137-145 (2005); Ye, Z. et al., Peptides, 26:2017-2025 (2005); Farooqi, I. S. et al., NE J Med., 348:1085-1095 (2003); MacNeil, D. J. et al., Eu. J. Pharm., 44:141-157 (2002); MacNeil, D. J. et al., Eu. J. Pharm., 450:93-109 (2002); Kask, A. et al., NeuroReport, 10:707-711 (1999); Schwartz, M. W., J. Clin. Invest., 108:963-964 (2001), Gura, T., Science, 287:1738-1740 (2000), Raffin-Sanson, M. L., Eu. J. Endo., 144:207-208 (2001), Hamilton, B. S. et al., Obesity Res. 10:182-187 (2002)), feeding disorders (U.S. Pat. No. 6,720,324; Fehm, H. L. et al., J. Clin. Endo. 2 Metab., 86:1144-1148 (2001); Pontillo, J. et al., Bioorganic 2 Med. Chem. Ltrs., 15:2541-2546 (2005)) and Prader-Willi Syndrome (G E, Y. et al., Brain Research, 957:42-45 (2002)); metabolic diseases and medical conditions accompanied by weight loss such as anorexia (U.S. Pat. No. 6,613,874; Wisse, B. R. et al., Endo., 142:3292-3301 (2001)), bulimia (U.S. Pat. No. 6,720,324), AIDS wasting (Marsilje, T. H. et al., Bioorg. Med. Chem. Lett., 14:3721-3725 (2004); Markison, S. et al., Endocrinology, 146:2766-2773 (2005)), cachexia (U.S. Pat. No. 6,613,874; Lechan, R. M. et al., Endo., 142:3288-3291 (2001); Pontillo, J. et al., Bioorganic 2 Med. Chem. Ltrs., 15:2541-2546 (2005)), cancer cachexia (U.S. Pat. No. 6,639,123) and wasting in frail elderly (U.S. Pat. No. 6,639,123); diabetes (U.S. Pat. No. 6,713,487) and diabetalogical related conditions and complications of diabetes such as retinopathy (U.S. Pat. No. 6,525,019); neoplastic proliferation (U.S. Pat. No. 6,713,487) such as skin cancer (Sturm, R. A., Melanoma Res., 12:405-416 (2002); Bastiens, M. T. et al., Am. J. Hum. Genet., 68:884-894 (2001)), and prostate cancer (Luscombe, C. J. et al., British J. Cancer, 85:1504-1509 (2001); reproductive or sexual medical conditions such as endometriosis (U.S. Pat. No. 6,713,487) and uterine bleeding in women (U.S. Pat. No. 6,613,874), sexual dysfunction (U.S. Pat. No. 6,720,324; Van der Ploeg, L. H. T. et al., PNAS, 99:11381-11386 (2002), Molinoff, P. B. et al., Ann. N.Y. Acad. Sci., 994:96-102 (2003), Hopps, C. V. et al., BJU International, 92:534-538 (2003)), erectile dysfunction ((U.S. Pat. No. 6,613,874; Diamond, L. E. et al., Urology, 65:755-759 (2005), Wessells, H. et al., Int. J. Impotence Res., 12:S74-S79 (2000), Andersson, K-E. et al., Int. J. Impotence Res., 14:S82-S92 (2002), Bertolini, A. et. al., Sexual Behavior: Pharmacology and Biochemistry, Raven Press, NY, p 247-257 (1975); Wessells, H. et al., Neuroscience, 118:755-762 (2003), Wessells, H. et al., Urology, 56:641-646 (2000), Shadiack, A. M. et al., Society for Neuroscience Abstract, (2003); Wessells, H. et al., J. Urology, 160:389-393 (1998), Rosen, R. C. et al., Int. J. Impotence Res., 16:135-142 (2004), Wessells, H. et al., Peptides, 26:1972-1977 (2005)) and decreased sexual response in females (U.S. Pat. No. 6,713,487; Fourcroy, J. L., Drugs, 63:1445-1457 (2003)); diseases or conditions resulting from treatment or insult to the organism such as organ transplant rejection (U.S. Pat. No. 6,713,487; Catania, A. et al., Pharm. Rev., 56:1-29 (2004)), ischemia and reperfusion injury (Mioni, C. et al., Eu. J. Pharm., 477:227-234 (2003); Catania, A. et al., Pharm. Rev., 56:1-29 (2004)), treatment of spinal cord injury and to accelerate wound healing (Sharma H. S. et al., Acta. Nerochir. Suppl., 86:399-405 (2003); Sharma H. S., Ann. N.Y. Acad. Sci. 1053: 407-421 (2005); U.S. Pat. No. 6,525,019), as well as weight loss caused by chemotherapy, radiation therapy, temporary or permanent immobilization (Harris, R. B. et al., Physiol. Behav., 73:599-608 (2001)) or dialysis; cardiovascular diseases or conditions such as hemorrhagic shock (Catania, A. et al., Pharm. Rev., 56:1-29 (2004)), cardiogenic shock (U.S. Pat. No. 6,613,874), hypovolemic shock (U.S. Pat. No. 6,613,874), cardiovascular disorders (U.S. Pat. No. 6,613,874) and cardiac cachexia (Markison, S. et al., Endocrinology, 146:2766-2773 (2005); pulmonary diseases or conditions such as acute respiratory distress syndrome (U.S. Pat. No. 6,350,430; Catania, A. et al., Pharm. Rev., 56:1-29 (2004)), chronic obstructive pulmonary disease (U.S. Pat. No. 6,713,487), asthma (U.S. Pat. No. 6,713,487) and pulmonary fibrosis; to enhance immune tolerance (Luger, T. A. et al., Pathobiology, 67:318-321 (1999)) and to combat assaults to the immune system such as those associated with certain allergies (U.S. Pat. No. 6,713,487) or organ transplant rejection (U.S. Pat. No. 6,713,487; Catania, A. et al., Pharm. Rev., 56:1-29 (2004)); treatment of dermatological diseases and conditions such as psoriasis (U.S. Pat. No. 6,713,487), skin pigmentation depletion (U.S. Pat. No. 6,713,487; Ye, Z. et al., Peptides, 26:2017-2025 (2005)), acne (Hatta, N. et al., J. Invest. Dermatol., 116:564-570 (2001); Bohm, M. et al., J. Invest. Dermatol., 118:533-539 (2002)), keloid formation (U.S. Pat. No. 6,525,019) and skin cancer (Sturm, R. A., Melanoma Res., 12:405-416 (2002); Bastiens, M. T. et al., Am. J. Hum. Genet., 68:884-894 (2001)); behavioral, central nervous system or neuronal conditions and disorders such as anxiety (U.S. Pat. No. 6,720,324; Pontillo, J. et al., Bioorganic 2 Med. Chem. Ltrs., 15:2541-2546 (2005)), depression (Chaki, S. et al., Peptides, 26:1952-1964 (2005), Bednarek, M. A. et al., Expert Opinion Ther. Patents, 14:327-336 (2004); U.S. Pat. No. 6,720,324), memory and memory dysfunction (U.S. Pat. No. 6,613,874; Voisey, J. et al., Curr. Drug Targets, 4:586-597 (2003)), modulating pain perception (U.S. Pat. No. 6,613,874; Bertolini, A. et al., J. Endocrinol. Invest., 4:241-251 (1981); Vrinten, D. et al., J. Neuroscience, 20:8131-8137 (2000)) and treating neuropathic pain (Pontillo, J. et al., Bioorganic 2 Med. Chem. Ltrs., 15:2541-2546 (2005)); conditions and diseases associated with alcohol consumption, alcohol abuse and/or alcoholism (WO 05/060985; Navarro, M. et al., Alcohol Clin. Exp. Res., 29:949-957 (2005)); and renal conditions or diseases such as the treatment of renal cachexia (Markison, S. et al., Endocrinology, 146:2766-2773 (2005)) or natriuresis (U.S. Pat. No. 6,613, 874).

Ligand compounds activating one or more melanocortin receptor would be useful for modulating a wide variety of normalizing or homeostatic activities in a subject in need thereof including thyroxin release (U.S. Pat. No. 6,613,874), aldosterone synthesis and release (U.S. Pat. No. 6,613,874), body temperature (U.S. Pat. No. 6,613,874), blood pressure (U.S. Pat. No. 6,613,874), heart rate (U.S. Pat. No. 6,613, 874), vascular tone (U.S. Pat. No. 6,613,874), brain blood flow (U.S. Pat. No. 6,613,874), blood glucose levels (U.S. Pat. No. 6,613,874), bone metabolism, bone formation or development (Dumont, L. M. et al., Peptides, 26:1929-1935 (2005), ovarian weight (U.S. Pat. No. 6,613,874), placental development (U.S. Pat. No. 6,613,874), prolactin and FSH secretion (U.S. Pat. No. 6,613,874), intrauterine fetal growth (U.S. Pat. No. 6,613,874), parturition (U.S. Pat. No. 6,613, 874), spermatogenesis (U.S. Pat. No. 6,613,874), sebum and pheromone secretion (U.S. Pat. No. 6,613,874), neuroprotection (U.S. Pat. No. 6,639,123) and nerve growth (U.S. Pat. No. 6,613,874) as well as modulating motivation (U.S. Pat. No. 6,613,874), learning (U.S. Pat. No. 6,613,874) and other behaviors (U.S. Pat. No. 6,613,874).

There exists a need for improved formulations of compositions containing peptides that are ligands of one or more of the melanocortin receptors, in particular ligands that selectively bind to MC4-R, that provide acceptable sustained release profile with improved pharmacokinetic parameters upon single subcutaneous injection. Ideally, such improved sustained release formulations comprise novel peptides that act as ligands for one or more of the melanocortin receptors as disclosed in the Applicant's own prior international publications WO2007/008704, WO2008/147556 and WO2008/156677. Moreover, among other therapeutic effects of the formulations of the present invention, are attenuated side effects and improved efficacy associated with flatter release profile. In addition, the present invention provides for a solution, which may or may not be a clear solution, devoid of excipients thus simplifying the manufacturing process.

SUMMARY OF THE INVENTION

The inventors of the present invention made a surprising discovery that a formulation of a pharmaceutical composition comprising a pamoate salt of a peptide that acts as a ligand of one or more of the melanocortin receptors exhibits an ideal solubility for slow release in vivo. Particularly preferred is the following peptide which is referred to hereinafter as "Example 1": Ac-Arg-cyclo(Cys-D-Ala-His-D-Phe-Arg-Trp-Cys)-NH$_2$, a ligand of the melanocortin receptor subtype 4, wherein after subcutaneous or intramuscular administration to a subject, the peptide forms a depot at physiological pH that is slowly dissolved and released into the body fluid and bloodstream, thereby resulting in attenuated side effects and improved efficacy.

The invention may be summarized in the following paragraphs below, as well as in the claims.

(1) In one aspect, the present invention is directed to a pharmaceutical composition of a solution, a gel or a semi-solid, or a suspension, comprising a peptide that acts as a ligand of one or more of the melanocortin receptors, or a pharmaceutically acceptable salt thereof, in which the peptide forms a depot after subcutaneous or intramuscular administration to a subject.

(2) The pharmaceutical composition according to paragraph 1, wherein said peptide in said solution forms a depot at an injection site after administration that is slowly dissolved and released into the body fluid and bloodstream, and wherein said solution is a purely aqueous solution, a purely organic solution, an aqueous solution having an organic component, an aqueous solution having an inorganic component, or an aqueous solution having both organic and inorganic components.

(3) The pharmaceutical composition according to paragraph 1 or paragraph 2, wherein said peptide is Example 1, i.e., Ac-Arg-cyclo(Cys-D-Ala-His-D-Phe-Arg-Trp-Cys)-NH$_2$.

(4) The pharmaceutical composition according to any one of the preceding paragraphs, wherein said peptide is in a pamoate salt form.

(5) The pharmaceutical composition according to any one of the preceding paragraphs, further comprising an organic component which increases the solubility of said peptide in an aqueous solution or decreases the viscosity of a gel or a semi-solid.

(6) The pharmaceutical composition according to paragraph 5, wherein said organic component is an organic polymer, an alcohol, DMSO, DMF, or DMA.

(7) The pharmaceutical composition according to paragraph 6, wherein said organic polymer is PEG.

(8) The pharmaceutical composition according to paragraph 7, wherein said PEG has an average molecular weight of from about 200 to about 10,000.

(9) The pharmaceutical composition according to paragraph 8, wherein said peptide is dissolved in a PEG200 or PEG400 aqueous solution, in which the volume-to-volume ratio of PEG to water is from about 1:99 to about 99:1.

(10) The pharmaceutical composition according to paragraph 9, wherein said peptide is dissolved in a PEG200 or PEG400 aqueous solution, in which the volume-to-volume ratio of PEG to water is from about 1:9 to about 1:1.

(11) The pharmaceutical composition according to paragraph 6, wherein said alcohol is ethanol or isopropyl alcohol.

(12) The pharmaceutical composition according to any one of the preceding paragraphs, wherein the weight-to-volume concentration of said peptide is between about 0.1 mg/mL and about 600 mg/mL.

(13) The pharmaceutical composition according to any one of the preceding paragraphs, wherein the pH of said composition is between about 3.0 and about 8.0.

(14) The pharmaceutical composition according to paragraph 13, wherein said pamoate salt of Arg-cyclo(Cys-D-Ala-His-D-Phe-Arg-Trp-Cys)-NH$_2$ is dissolved in a PEG400/aqueous solution, in which the volume-to-volume ratio of PEG400 to water is about 1:1, and in which the weight-to-volume concentration of the peptide is about 200 mg/mL.

(15) The pharmaceutical composition according to paragraph 13, wherein said pamoate salt of Arg-cyclo(Cys-D-Ala-His-D-Phe-Arg-Trp-Cys)-NH$_2$ is dissolved in a PEG200/aqueous solution, in which the volume-to-volume ratio of PEG200 to water is about 1:1, and in which the weight-to-volume concentration of the peptide is about 200 mg/mL.

(16) The pharmaceutical composition according to paragraph 13, wherein said pamoate salt of Arg-cyclo(Cys-D-Ala-His-D-Phe-Arg-Trp-Cys)-NH$_2$ is dissolved in a PEG400/PBS solution, in which the volume-to-volume ratio of PEG400 to PBS is about 1:1, and in which the weight-to-volume concentration of the peptide is about 300 mg/mL.

(17) The pharmaceutical composition according to paragraph 13, wherein said pamoate salt of Arg-cyclo(Cys-D-Ala-His-D-Phe-Arg-Trp-Cys)-NH$_2$ is dissolved in a PEG400/saline solution, in which the volume-to-volume ratio of PEG400 to saline solution is about 1:1, and in which the weight-to-volume concentration of the peptide is about 300 mg/mL.

(18) The pharmaceutical composition according to any one of the preceding paragraphs, further comprising a preservative.

(19) The pharmaceutical composition according to paragraph 18, wherein said preservative is selected from the group consisting of m-cresol, phenol, benzyl alcohol, and methyl paraben.

(20) The pharmaceutical composition according to paragraph 19, wherein said preservative is present in a concentration from about 0.01 mg/mL to about 100 mg/mL.

(21) The pharmaceutical composition according to any one of the preceding paragraphs, further comprising an isotonic agent.

(22) The pharmaceutical composition according to paragraph 21, wherein said isotonic agent is present in a concentration from about 0.01 mg/mL to about 100 mg/mL.

(23) The pharmaceutical composition according to any one of the preceding paragraphs, further comprising a stabilizer.

(24) The pharmaceutical composition according to paragraph 23, wherein said stabilizer is selected from the group consisting of imidazole, arginine and histidine.

(25) The pharmaceutical composition according to any one of the preceding paragraphs, further comprising a surfactant.

(26) The pharmaceutical composition according to any one of the preceding paragraphs, further comprising a chelating agent.

(27) The pharmaceutical composition according to any one of the preceding paragraphs, further comprising a buffer.

(28) The pharmaceutical composition according to paragraph 27, wherein said buffer is selected from the group consisting of Tris, ammonium acetate, sodium acetate, glycine, aspartic acid, and Bis-Tris.

(29) The pharmaceutical composition according to any one of the preceding paragraphs, further comprising a divalent metal.

(30) The pharmaceutical composition according to paragraph 29, wherein said divalent metal is zinc.

(31) The pharmaceutical composition according to any one of the preceding paragraphs, wherein said solution is a clear solution.

Although the preferred embodiment of the present invention is directed to Example 1, i.e., Ac-Arg-cyclo(Cys-D-Ala-His-D-Phe-Arg-Trp-Cys)-NH$_2$, which is a ligand of MCR-R, the present invention is in no way limited to Example 1. The peptides of the present invention include, for example, all those peptides that act as ligands for one or more of the melanocortin receptors, as disclosed in the applicant's own prior international publication numbers published as WO2007/008704, WO2008/147556 and WO2008/156677. These publications are herein incorporated by reference to the same extent as if the disclosure of each independent publication was explicitly provided herein.

The following compounds from these publications may also be advantageously employed to constitute the pharmaceutical compositions of the present invention:

Example 2: Ac-D-Arg-cyclo(Cys-D-Ala-His-D-Phe-Arg-Trp-Cys)-NH$_2$;

Example 3: Ac-Tyr-Arg-cyclo(Cys-D-Ala-His-D-Phe-Arg-Trp-Cys)-NH$_2$;

Example 4: Ac-Tyr-D-Arg-cyclo(Cys-D-Ala-His-D-Phe-Arg-Trp-Cys)-NH$_2$; and

Example 5: hydantoin(Arg-Gly)-cyclo(Cys-Glu-His-D-Phe-Arg-Trp-Cys)-NH$_2$.

DETAILED DESCRIPTION OF THE INVENTION

The nomenclature used to define the peptides herein is that typically used in the art wherein the amino group at the N-terminus appears to the left and the carboxyl group at the C-terminus appears to the right. Where the amino acid has isomeric forms, it is the L form of the amino acid that is represented unless otherwise explicitly indicated. Unless defined otherwise, all technical and scientific terms used herein have the same meaning as commonly understood by one of ordinary skill in the art to which this invention belongs.

Abbreviations used herein are defined as follows:

Ac: acetyl

Ala or A: alanine

Arg or R: arginine

Cys or C: cysteine

Glu or E: glutamic acid

Gly or G: glycine

His or H: histidine

Phe or F: phenylalanine

Trp or W: tryptophan

Tyr or Y: tyrosine

Unless otherwise indicated, all abbreviations (e.g., Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system.

The designation "NH$_2$" in, e.g., Ac-Arg-cyclo(Cys-D-Ala-His-D-Phe-Arg-Trp-Cys)-NH$_2$, indicates that the C-terminus of the peptide is amidated.

"-cyclo(Cys-Cys)-" denotes the structure:

The term "about" as used herein, in associations with parameters and amounts, means that the parameter or amount is within ±5% of the stated parameter or amount.

Certain other abbreviations used herein are defined as follows:
Boc: tert-butyloxycarbonyl
BSA: bovine serum albumin
DCM: dichloromethane
DIPEA: diisopropylethylamine
DMF: dimethylformamide
DTT: dithiothrieitol
Fmoc: 9-Fluorenylmethyloxycarbonyl
HBTU: 2-(1H-benzotriazole-1-yl)-1,1,3,3-tetramethyluronium hexafluorophosphate
HOBt: 1-hydroxy-benzotriazole
HPLC: high performance liquid chromatography
IBMX: isobutylmethylxanthine
Sodium pamoate: pamoic acid disodium salt having the structure of LC-MS: liquid chromatography mass spectrometry
LOQ: limit of quantification
MRM: multiple reaction monitoring
NMP: N-methylpyrrolidone
PBS: phosphate buffered saline
PEG: poly(ethylene glycol), which has the structure of wherein n an integer between 1 and 2,000
PEG200: poly(ethylene glycol) with an average molecular weight of about 200 Da
PEG400: poly(ethylene glycol) with an average molecular weight of about 400 Da
TFA: trifluoroacetic acid
TIS: triisopropylsilane
Tris-HCl: tris(hydroxymethyl)aminomethane hydrochloride
Trt: trityl

SYNTHESIS

The peptides of this invention can be prepared by standard solid phase peptide synthesis. See, e.g., Stewart, J. M., et al., *Solid Phase Synthesis* (Pierce Chemical Co., 2d ed. 1984). The following examples describe synthetic methods for making a peptide of this invention, which methods are well-known to those skilled in the art. Other methods are also known to those skilled in the art. The examples are provided for the purpose of illustration and are not meant to limit the scope of the present invention in any manner Synthesis of Example 1 i.e., Ac-Arg-cyclo(Cys-D-Ala-His-D-Phe-Arg-Trp-Cys)-NH$_2$

The title peptide having the above structure was assembled using Fmoc chemistry on an Apex peptide synthesizer (Aapptec; Louisville, Ky., USA). 220 mg of 0.91 mmol/g (0.20 mmoles) Rink Amide MBHA resin (Polymer Laboratories; Amherst, Mass., USA) was placed in a reaction well and pre-swollen in 3.0 mL of DMF prior to synthesis. For cycle 1, the resin was treated with two 3-mL portions of 25% piperidine in DMF for 5 and 10 minutes respectively, followed by 4 washes of 3-mL DMF—each wash consisting of adding 3 mL of solvent, mixing for 1 minute, and emptying for 1 minute. Amino acids stocks were prepared in NMP as 0.45M solutions containing 0.45M HOBT. HBTU was prepared as a 0.45M solution in NMP and DIPEA was prepared as a 2.73M solution in NMP. To the resin, 2 mL of the first amino acid (0 9 mmoles, Fmoc-Cys(Trt)-OH) (Novabiochem; San Diego, Calif., USA) was added along with 2 mL (0.9 mmoles) of HBTU and 1.5 mL (4.1 mmoles) of DIPEA. After one hour of constant mixing, the coupling reagents were drained from the resin and the coupling step was repeated. Following amino acid acylation, the resin was washed with two 3-mL aliquots of DMF for 1 minute. The process of assembling the peptide (deblock/wash/acylate/wash) was repeated for cycles 2-9 identical to that as described for cycle 1. The following amino acids were used: cycle 2) Fmoc-Trp(Boc)-OH (Genzyme; Cambridge, Mass., USA); cycle 3) Fmoc-Arg(Pbf)-OH (Novabiochem); cycle 4) Fmoc-DPhe-OH (Genzyme); cycle 5) Fmoc-His(Trt)-OH (Novabiochem); cycle 6) Fmoc-D-Ala-OH (Genzyme); cycle 7) Fmoc-Cys(Trt)-OH, (Novabiochem); and cycle 8) Fmoc-Arg(Pbf)-OH (Genzyme). The N-terminal Fmoc was removed with 25% piperidine in DMF as described above, followed by four 3-mL DMF washes for 1 minute. Acetylation of the N-terminus was performed by adding 0.5 mL of 3M DIPEA in NMP to the resin along with 1.45 mL of 0.45M acetic anhydride in NMP. The resin was mixed for 30 minutes and acetylation was repeated. The resin was washed with 3 mL of DMF for a total of 5 times followed with 5 washes with 5 mL of DCM each.

To cleave and deprotect the peptide, 5mL of the following reagent was added to the resin: 2% TIS/5% water/5% (w/v) DTT/88% TFA. The solution was allowed to mix for 3.5 hours. The filtrate was collected into 40 mL of cold anhydrous ethyl ether. The precipitate was pelleted for 10 minutes at 3500 rpm in a refrigerated centrifuge. The ether was decanted and the peptide was re-suspended in fresh ether. The ether workup was performed three times. Following the last ether wash, the peptide was allowed to air dry to remove residual ether.

The peptide was dissolved in 10% acetonitrile and analyzed by mass spectrometry and reverse-phase HPLC employing a 30×4.6 cm C18 column (Vydac; Hesperia, Calif., USA) with a gradient of 2-60% acetonitrile (0.1% TFA) over 30 minutes. This analysis identified a product with ~53% purity. Mass analysis employing electrospray ionization identified a main product containing a mass of 1118.4 corresponding to the desired linear product. The crude product (~100 mg) was diluted to a concentration of 2 mg/mL in 5% acetic acid. To this solution, 0.5M iodine/methanol was added dropwise with vigorous stirring until a pale yellow color was achieved. The solution was vigorously stirred for another 10 minutes. Excess iodine was then quenched by adding 1.0M sodium thiosulfate under continuous mixing until the mixture was rendered colorless. The peptide was re-examined by mass spectrometry analysis and HPLC. Mass spectrometry analysis identified a main species with a mass of 1116.4 which indicated successful oxidation to form the cyclic peptide. The peptide solution was purified on a preparative HPLC equipped with a C18 column using a similar elution gradient. The purified product was re-analyzed by HPLC for purity (>95%) and mass spectrometry (1116.9 which is in agreement with the expected mass of 1117.3) and subsequently lyophilized. Following lyophilization, 28 mg of purified product was obtained representing a 24% yield.

The other exemplified peptides were synthesized substantially according to the procedure described for the above-described synthetic process. Physical data for select exemplified peptides are given in Table 1.

TABLE 1

| Example Number | Mol. Wt. (calculated) | Mol. Wt. (ES-MS) | Purity (HPLC) |
|---|---|---|---|
| 1 | 1117.3 | 1116.9 | 95.1% |
| 2 | 1117.3 | 1116.8 | 99.2% |
| 3 | 1280.5 | 1280.6 | 98.0% |
| 5 | 1216.37 | 1216.20 | 99.9% |

Preparation of Pamoate Salt of Example 1

The acetate salt of Example 1 (200 mg, 0.18 mmole) was dissolved in 10 mL of water. Sodium pamoate (155 mg, 0.36 mmole) was dissolved in 10 mL of water. The two solutions were combined and mixed well. The precipitates were collected by centrifugation at 3000 rpm for 20 minutes, washed for three times with water, and dried by lyophilization.

In Vitro Studies

Compounds of the present invention can be and were tested for activity as ligands of one or more of the melanocortin receptors according to the following procedures. One skilled in the art would know that procedures similar to those described herein may be used to assay the binding activities of the compounds of the invention to melanocortin receptor molecules.

Radioligand Binding Assays

Cellular membranes used for the in vitro receptor binding assays were obtained from transgenic CHO-K1 cells stably expressing hMC-R receptor subtypes 1, 3, 4 or 5. The CHO-K1 cells expressing the desired hMC-R receptor type were sonicated (Branson®, CT, USA; setting 7, approximately 30 sec) in ice-cold 50 mM Tris-HCl at pH 7.4 and then centrifuged at 39,000 g for 10 minutes at a temperature of approximately 4° C. The pellets were resuspended in the same buffer and centrifuged at 50,000 g for 10 minutes at a temperature of approximately 4° C. The washed pellets containing the cellular membranes were stored at approximately −80° C.

Competitive inhibition of $[^{125}I](Tyr^2)$-$(Nle^4$-D-Phe$^7)\alpha$-MSH ($[^{125}I]$-NDP-$\alpha$-MSH; Amersham Biosciences®, Piscataway, N.J., USA) binding was carried out in polypropylene 96 well plates. Cell membranes (1-10 µg protein/well), prepared as described above, were incubated in 50 mM Tris-HCl at pH 7.4 containing 0.2% BSA, 5 mM $MgCl_2$, 1 mM $CaCl_2$ and 0.1 mg/mL bacitracin, with increasing concentrations of the test compound and 0.1-0.3 nM $[^{125}I]$-NDP-$\alpha$-MSH for approximately 90-120 minutes at approximately 37° C. Bound $[^{125}I]$-NDP-$\alpha$-MSH ligand was separated from free $[^{125}I]$-NDP-$\alpha$-MSH by filtration through GF/C glass fiber filter plates (Unifilter®, Meriden, Conn., USA) pre-soaked with 0.1% (w/v) polyethylenimine (PEI), using a Packard Filtermate® harvester (Millipore, Danvers, Mass., USA). Filters were washed three times with 50 mM Tris-HCl at pH 7.4 at a temperature of approximately 0-4° C. and then assayed for radioactivity using a Packard Topcount® scintillation counter (GMI, Inc., Ramsey, Minn., USA). Binding data were analyzed by computer-assisted non-linear regression analysis (XL fit; IDBS, Burlington, Mass., USA).

A selection of the preferred embodiments was tested using the above-discussed assay and the binding constants (Ki in nM) are reported in Table 2.

TABLE 2

| Example Number | Ki (nM) hMC1-R | Ki (nM) hMC3-R | Ki (nM) hMC4-R | Ki (nM) hMC5-R |
|---|---|---|---|---|
| 1 | 3.87 | 10.1 | 2.09 | 430 |
| 2 | 4.01 | 12.1 | 1.76 | 352 |
| 3 | 8.53 | 21.2 | 3.72 | 714 |
| 5 | 8.59 | 94.1 | 2.44 | 7760 |

Cyclic AMP Bioassay

Intracellular cyclic AMP (cAMP) levels were determined by an electrochemiluminescence (ECL) assay (Meso Scale Discovery, Gaithersburg, Md., USA; referred to hereinafter as "MSD"). CHO-K1 cells stably expressing the hMC receptor subtypes were suspended in RMPI 1640® assay buffer (RMPI 1640 buffer contains 0.5 mM IBMX, and 0.2% protein cocktail (MSD blocker A)). Transgenic CHO-K1 cells stably expressing hMC receptor subtypes 1, 3, 4 or 5 were dispensed at a density of approximately 7,000 cells/well in 384-well Multi-Array plates (MSD) containing integrated carbon electrodes and coated with anti-cAMP antibody. Increasing concentrations of the test compounds were added and the cells were incubated for approximately 40 minutes at approximately 37° C. Following this incubation, lysis buffer (HEPES-buffered saline solution with $MgCl_2$ and Triton X-100® at ph 7.3) containing 0.2% protein cocktail and 2.5 nM TAG™ ruthenium-labeled cAMP (MSD) was added and the cells were incubated for approximately 90 minutes at room temperature. At the end of the second incubation period, read buffer (Tris-buffered solution containing an ECL co-reactant and Triton X-100 at ph 7.8) was added and the cAMP levels in the cell lysates were immediately determined by ECL detection with a Sector Imager 6000 reader® (MSD). Data were analyzed using a computer-assisted non-linear regression analysis (XL fit; IDBS) and reported as either an $EC_{50}$ value or a Kb value.

$EC_{50}$ represents the concentration of an agonist compound needed to obtain 50% of the maximum reaction response, e.g., 50% of the maximum level of cAMP as determined using the assay described above. The Kb value reflects the potency of an antagonist and is determined by Schild analysis. In brief, concentration-response curves of an agonist are carried out in the presence of increasing concentrations of an antagonist. The Kb value is the concentration of antagonist which would produce a 2-fold shift in the concentration-response curve for an agonist. It is calculated by extrapolating the line on a Schild plot to zero on the y-axis.

A selection of compounds was tested using the above-discussed assays and the results are reported in Table 3.

TABLE 3

| Example Number | $EC_{50}$ hMC1-R | $EC_{50}$ hMC3-R | $EC_{50}$ hMC4-R | $EC_{50}$ hMC5-R |
|---|---|---|---|---|
| 1 | 5.79 | 5.25 | 0.313 | 1630 |
| 2 | 6.17 | 5.6 | 0.397 | 1020 |
| 3 | 6.42 | 2.39 | 0.194 | 1540 |
| 5 | 8.83 | 7.86 | 0.0979 | 4010 |

Solubility Studies

Preparation of Formulation of Pamoate Salt of Example 1

Pamoate salt of Example 1 (50 mg) was weighted into a microcentrifuge tube, and 125 µL of PEG400 and 125 µL of water were added thereafter. The mixture was sonicated to facilitate dissolution. A clear solution may be, and was, obtained.

The solubility of acetate salt of Example 1 was determined by weighing a certain amount of the peptide and dissolving it in a proper volume of water, saline, or PBS, and the results are shown in Table 4A.

TABLE 4A

| Solvent | Concentration (w/v) | pH | $ZnCl_2$ | Solubility |
|---|---|---|---|---|
| Water | 10% | 7.0 | no | soluble |
| Water | 10% | 7.0 | 1:1 molar | soluble |
| Water | 20% | 7.0 | no | soluble |
| Water | 20% | 7.0 | 1:1 molar | soluble |
| Water | 50% | 7.0 | no | soluble |
| Water | 50% | 7.0 | 1:1 molar | soluble |
| Water | 70% | 7.0 | no | soluble |
| Water | 70% | 7.0 | 1:1 molar | soluble |
| Water | 90% | 7.0 | no | soluble |
| Water | 90% | 7.0 | 1:1 molar | soluble |
| Water | 50% | 8.0 | no | soluble |
| Saline | 50% | 7.0 | no | soluble |
| Saline | 50% | 7.0 | 1:1 molar | soluble |
| Saline | 50% | 8.0 | no | soluble |
| PBS | 50% | 7.0 | no | soluble |
| PBS | 50% | 7.0 | 1:1 molar | soluble |
| PBS | 50% | 8.0 | no | soluble |

The solubility of pamoate salt of Example 1 was determined by mixing the peptide in water or PBS, followed by HPLC determination of the concentration in the supernatant, and the results are shown in Table 4B.

TABLE 4B

| Solubility of | Water, pH 7.0 | PBS, pH 7.4 |
|---|---|---|
| Pamoate salt of Example 1 | 0.06 mg/mL | 0.21 mg/mL |
| Pamoate salt of Example 1 with Zn | 0.05 mg/mL | 0.12 mg/mL |

Pharmacokinetic Studies of Formulations of Fatty Acid Salts of Example 1 in

The following "Formulations 1-6" of Example 1 were prepared:

(1) "Formulation 1": Pamoate salt of Example 1 dissolved in a 50% PEG400 and 50% water (v/v) solution, at a concentration of 200 mg/mL (20% w/v).

(2) "Formulation 2": Pamoate salt of Example 1 dissolved in a 50% PEG200 and 50% water (v/v) solution, at a concentration of 200 mg/mL (20% w/v).

(3) "Formulation 3": Pamoate salt of Example 1 dissolved in a 50% PEG400 and 50% PBS (v/v) solution, at a concentration of 300 mg/mL (30% w/v).

(4) "Formulation 4": Pamoate salt of Example 1 dissolved in a 50% PEG400 and 50% saline (v/v) solution, at a concentration of 300 mg/mL (30% w/v).

(5) "Formulation 5": Acetate salt of Example 1 dissolved in a saline/2% heat inactivated mouse serum/5% DMA/2% tween-80 solution.

Dosing

For Formulations 1 and 2, Sprague-Dawley rats were dosed via subcutaneous injection at a fixed amount of either 5 µL/rat or 1.0 mg/rat, or a variable amount of 2.5 mg/kg body weight.

For Formulations 3 and 4, Sprague-Dawley rats were dosed via subcutaneous injection at a fixed amount of either 5 μL/rat or 1.5 mg/rat, or a variable amount of 3.75 mg/kg body weight.

For Formulation 5, Sprague-Dawley rats were dosed via subcutaneous injection at a variable amount of 0.5 mg/kg body weight.

Sample Preparation

For Formulations 1 and 2, 100 μL of plasma was acidified with 5 μL of formic acid and precipitated with 300 μL of acetonitrile. The supernatant was collected by centrifugation and dried by speed-vac. The dried pellet was dissolved in 100 μL of water which was then centrifuged. 50 μL of the preparation was injected for LC-MS/MS analysis.

For Formulations 3 and 4, 200 μL of plasma was acidified with 10 μL of formic acid and precipitated with 600 μL of acetonitrile. The supernatant was collected by centrifugation and dried by speed-vac. The dried pellet was dissolved in 150 μL of water which was then centrifuged. 50 μL of the preparation was injected for LC-MS/MS analysis.

For Formulation 5, 200 μL of plasma was acidified with 10 μL of formic acid and precipitated with 600 μL of acetonitrile. The supernatant was collected by centrifugation and dried by speed-vac. The dried pellet was dissolved in 150 μL of 30% acetonitrile which was then centrifuged. 50 μL of the preparation was injected for LC-MS/MS analysis.

LC-MS/MS Analysis

For Formulations 1 and 2, LC-MS/MS analysis was performed with an API4000 mass spectrometer system equipped with a Turbo Ionspray probe. The MRM mode of molecular ion detection with an ion pair of 559.5 and 110.1 was used. HPLC separation was performed with a Luna C8(2) 2×30 mm 3μ column run from 0% B to 80% B in 10 minutes at a flow rate of 0.3 mL/minute. Buffer A is 1% formic acid in water and buffer B is 1% formic acid in acetonitrile. LOQ was 5 ng/mL.

For Formulations 3 and 4, LC-MS/MS analysis was performed with an API4000 mass spectrometer system equipped with a Turbo Ionspray probe. The MRM mode of molecular ion detection with an ion pair of 559.5 and 110.1 was used. HPLC separation was performed with a Luna C8(2) 2×30 mm 3μ column run from 0% B to 80% B in 10 minutes at a flow rate of 0.3 mL/minute. Buffer A is 1% formic acid in water and buffer B is 1% formic acid in acetonitrile. LOQ was 2 ng/mL.

For Formulation 5, LC-MS/MS analysis was performed with an API4000 mass spectrometer system equipped with a Turbo Ionspray probe. The MRM mode of molecular ion detection with an ion pair of 559.5 and 110.1 was used. HPLC separation was performed with a Luna C8(2) 2×30 mm 3μ column run from 0% B to 90% B in 10 minutes at a flow rate of 0.3 mL/minute. Buffer A is 1% formic acid in water and buffer B is 1% formic acid in acetonitrile. LOQ was 1 ng/mL.

Results and Summary

The plasma concentrations of Example 1, dosed with the Formulations 1-5, were calculated with its standard calibration plot and the results are shown in Table 5.

TABLE 5

| Time | Plasma concentration (ng/mL) of Example 1, dosed with Formulation 1 | Plasma concentration (ng/mL) of Example 1, dosed with Formulation 2 | Plasma concentration (ng/mL) of Example 1, dosed with Formulation 3 | Plasma concentration (ng/mL) of Example 1, dosed with Formulation 4 | Plasma concentration (ng/mL) of Example 1, dosed with Formulation 5 |
|---|---|---|---|---|---|
| 5 minutes | 55.35 | 84.40 | 44.1 | 56.0 | 83.8 |
| 10 minutes | 57.05 | 153.50 | 69.5 | 84.0 | 200.7 |
| 15 minutes | 83.65 | 187.50 | 94.7 | 109.0 | 245.0 |
| 30 minutes | 94.80 | 212.00 | 165.0 | 150.7 | 298.3 |
| 1 hour | 123.00 | 237.00 | N/A | 193.0 | 292.0 |
| 2 hours | 127.00 | 304.50 | 559.7 | 269.0 | 160.7 |
| 3 hours | N/A | N/A | N/A | N/A | 72.4 |
| 4 hours | 182.50 | 420.00 | 768.3 | 644.5 | 38.4 |
| 5 hours | N/A | N/A | N/A | N/A | 16.6 |
| 8 hours | 135.00 | 235.50 | 478.7 | 495.0 | N/A |
| 12 hours | 71.30 | 86.00 | 239.0 | 167.5 | N/A |
| 16 hours | 42.85 | 42.25 | 142.5 | 181.0 | N/A |
| 20 hours | 24.30 | 31.60 | 112.8 | 68.0 | N/A |
| 24 hours | 16.50 | 27.85 | 86.9 | 75.9 | N/A |

Figure 1A:
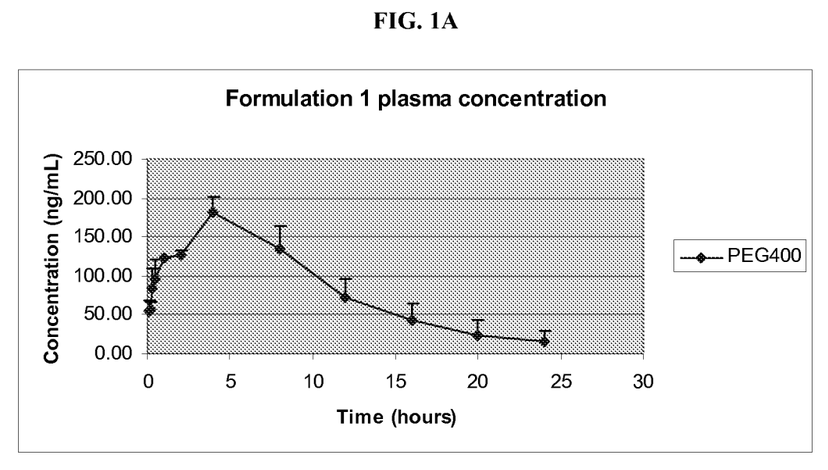
FIG. 1A and FIG. 1B show full time course plots of the pharmacokinetic profiles (median values) obtained after a single subcutaneous administration to Sprague-Dawley rats dosed at 2.5 mg/kg body weight, of a formulation comprising 200 mg/mL (20% w/v) of pamoate salt of Example 1 dissolved in a 50% PEG400 and 50% water (v/v) solvent, on a normal scale and on a logarithmic scale, respectively.
Figure 1B:
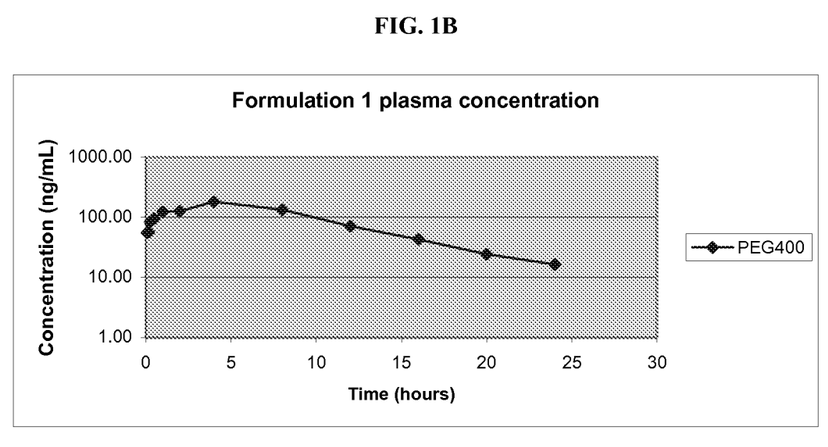

Full time course plots of the pharmacokinetic profiles of Formulation 1 are shown on a normal scale in FIG. 1A, and on a logarithmic scale in FIG. 1B.

Figure 2A:
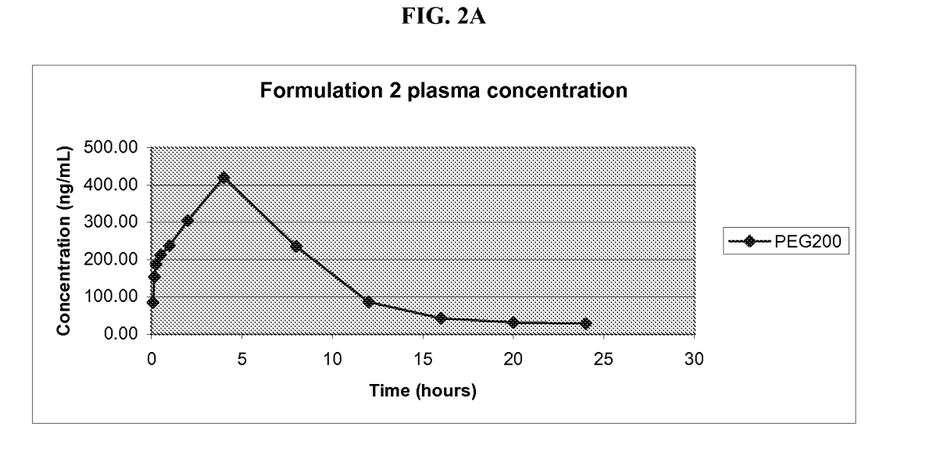
FIG. 2A and FIG. 2B show full time course plots of the pharmacokinetic profiles (median values) obtained after a single subcutaneous administration to Sprague-Dawley rats dosed at 2.5 mg/kg body weight, of a formulation comprising 200 mg/mL (20% w/v) of pamoate salt of Example 1 dissolved in a 50% PEG200 and 50% water (v/v) solvent, on a normal scale and on a logarithmic scale, respectively.
Figure 2B:
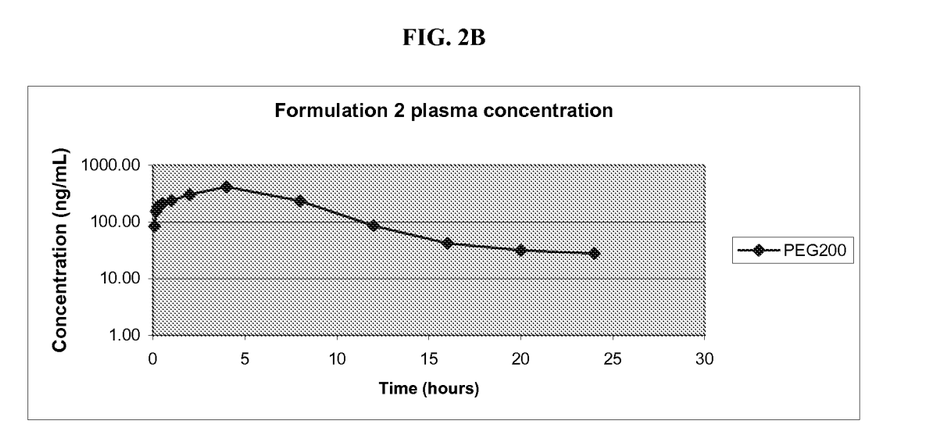

Full time course plots of the pharmacokinetic profiles of Formulation 2 are shown on a normal scale in FIG. 2A, and on a logarithmic scale in FIG. 2B.

Figure 3A:
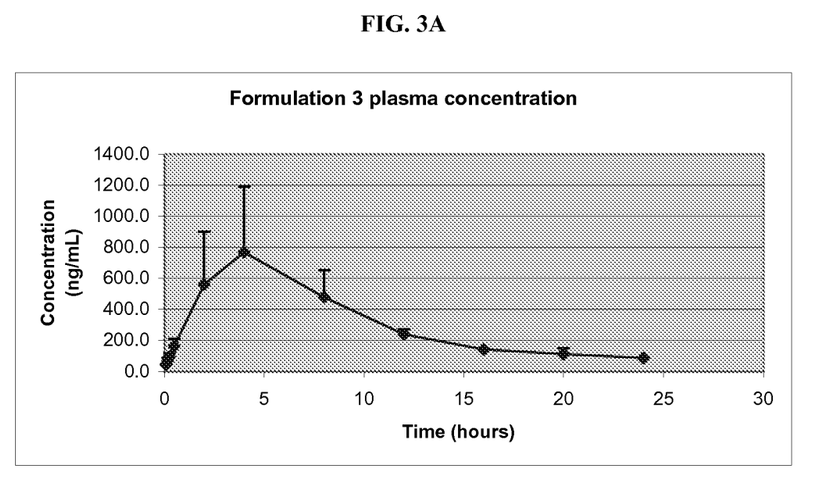
FIG. 3A and FIG. 3B show full time course plots of the pharmacokinetic profiles (median values) obtained after a single subcutaneous administration to Sprague-Dawley rats dosed at 3.75 mg/kg body weight, of a formulation comprising 300 mg/mL (30% w/v) of pamoate salt of Example 1 dissolved in a 50% PEG400 and 50% PBS (v/v) solvent, on a normal scale and on a logarithmic scale, respectively.
Figure 3B:
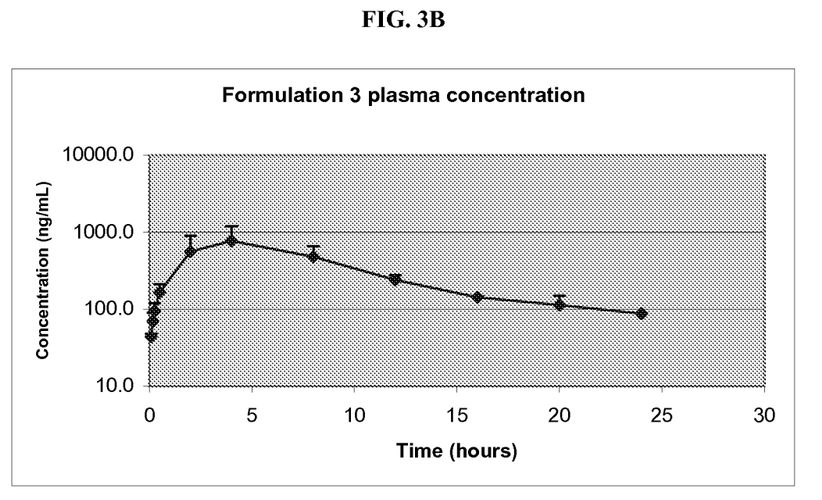

Full time course plots of the pharmacokinetic profiles of Formulation 3 are shown on a normal scale in FIG. 3A, and on a logarithmic scale in FIG. 3B.

Figure 4A:
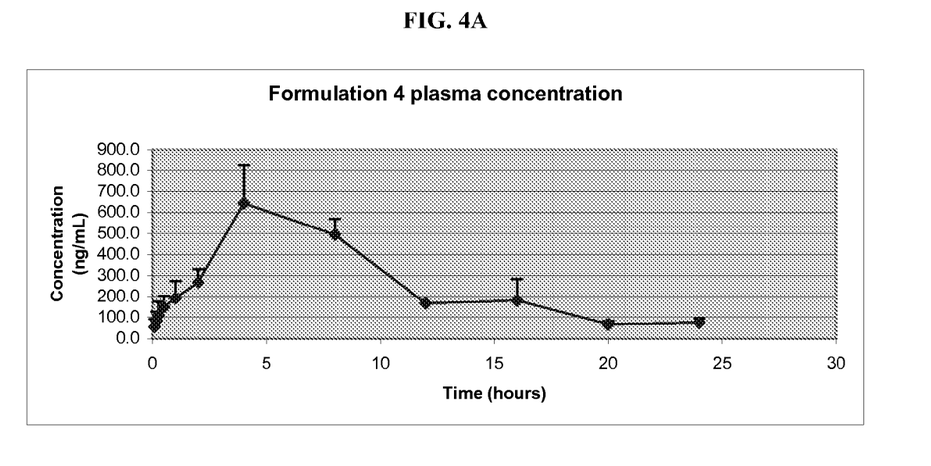
FIG. 4A and FIG. 4B show full time course plots of the pharmacokinetic profiles (median values) obtained after a single subcutaneous administration to Sprague-Dawley rats dosed at 3.75 mg/kg body weight, of a formulation comprising 300 mg/mL (30% w/v) of pamoate salt of Example 1 dissolved in a 50% PEG400 and 50% saline (v/v) solvent, on a normal scale and on a logarithmic scale, respectively.
Figure 4B:
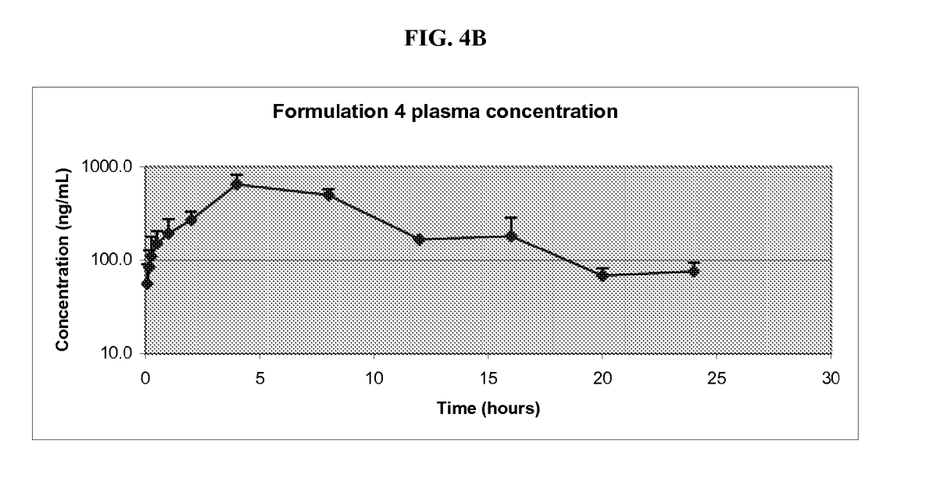

Full time course plots of the pharmacokinetic profiles of Formulation 4 are shown on a normal scale in FIG. 4A, and on a logarithmic scale in FIG. 4B.

Figure 5A:
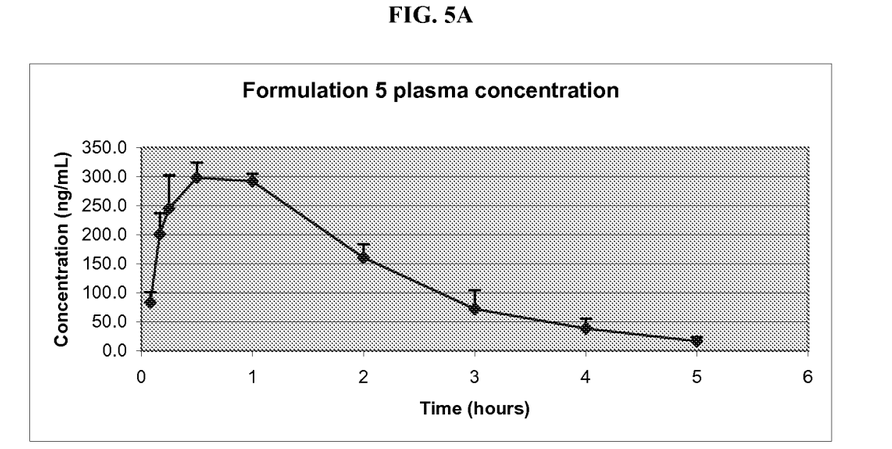
FIG. 5A and FIG. 5B show full time course plots of the pharmacokinetic profiles (median values) obtained after a single subcutaneous administration to Sprague-Dawley rats dosed at 0.5 mg/kg body weight of a formulation comprising acetate salt of Example 1 dissolved in a saline/2% heat inactivated mouse serum/5% DMA/2% tween-80 solvent, on a normal scale and on a logarithmic scale, respectively.
Figure 5B:
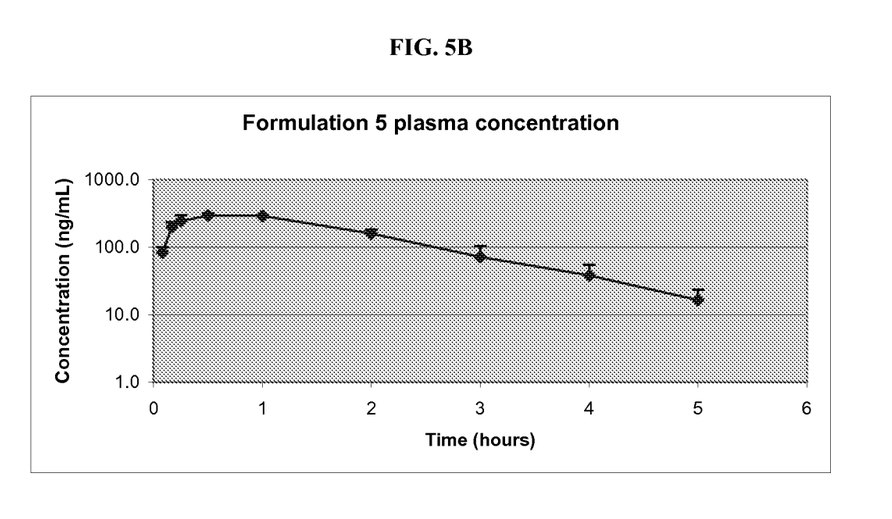

Full time course plots of the pharmacokinetic profiles of Formulation 5 are shown on a normal scale in FIG. 5A, and on a logarithmic scale in FIG. 5B.

Figure 6A:
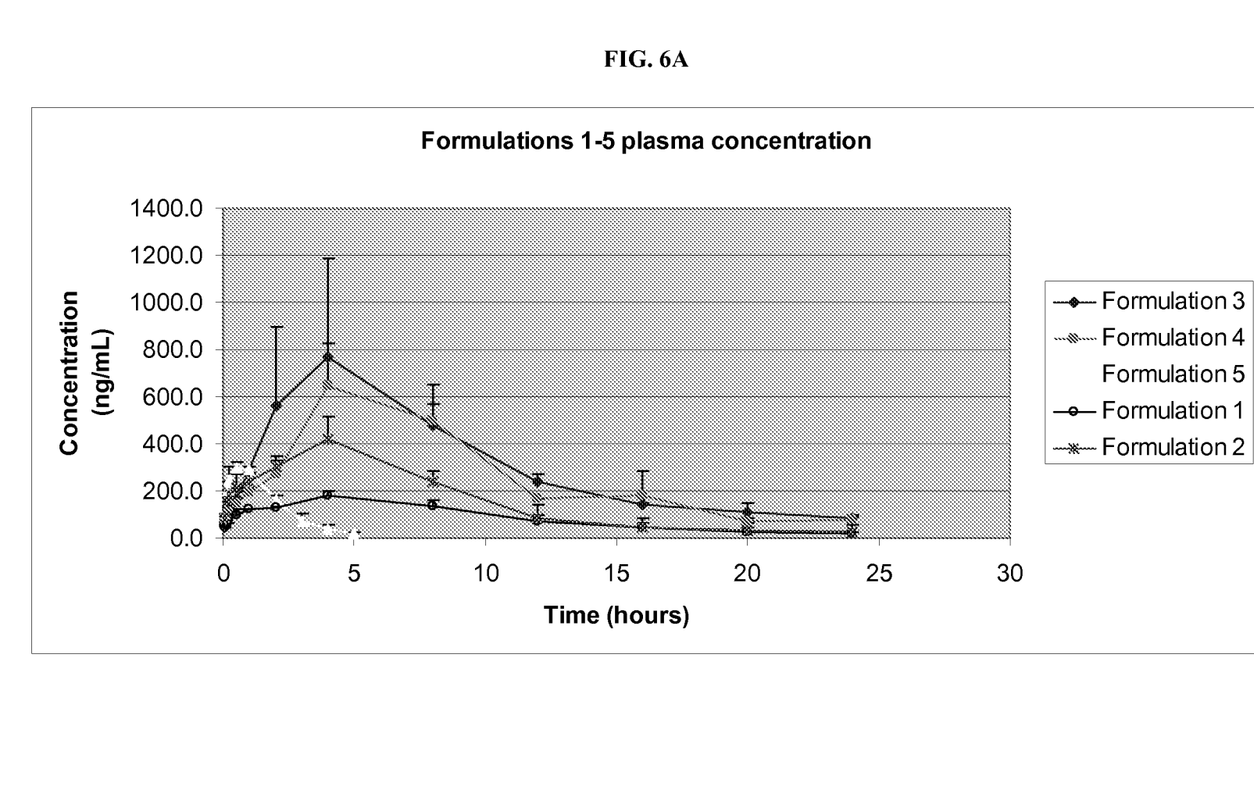
FIGS. 6A and 6B show the same full time course plots of the pharmacokinetic profiles (median values) as shown in FIG. 1A through FIG. 5A on a normal scale as well as FIG. 1B through 5B on a logarithmic scale as a side-by-side comparison of the different formulations used in the experiments as described herein.
Figure 6B:
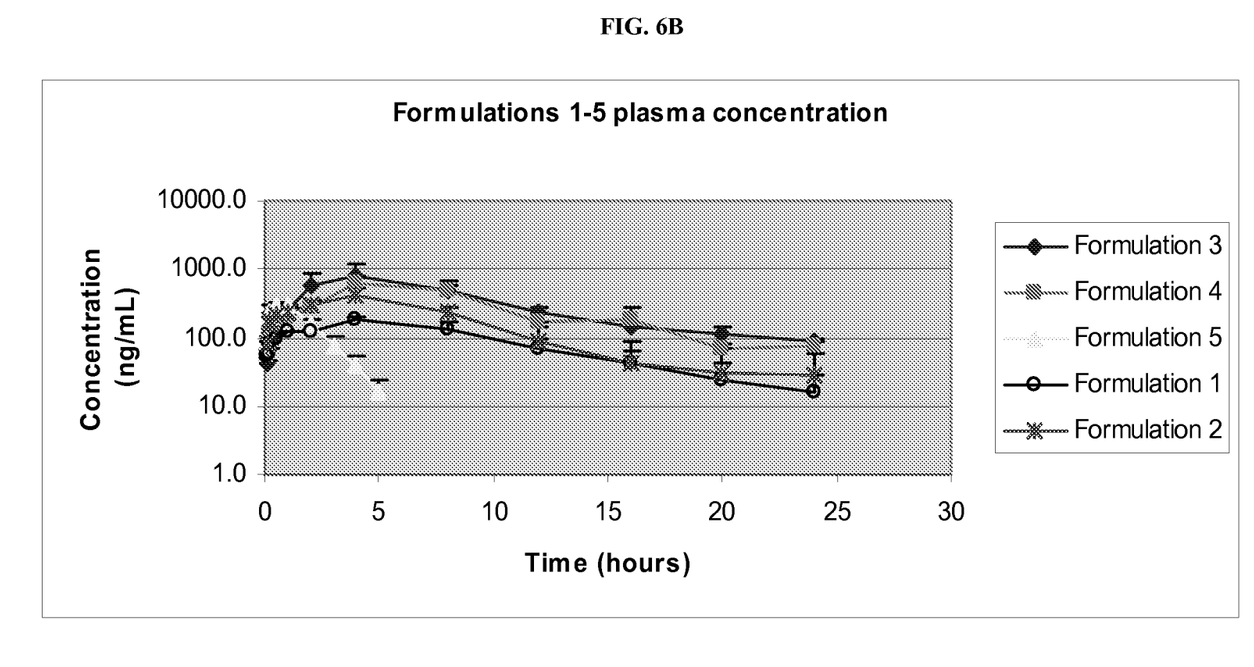

FIG. 6A and 6B show the same full time course plots of the pharmacokinetic profiles (median values) as shown in FIG. 1A through FIG. 5A on a normal scale, as well as FIG. 1B through 5B on a logarithmic scale, as a side-by-side comparison of the different formulations used in the experiments as described herein.

Some pharmacokinetic parameters of Example 1, dosed with the Formulations 1-5, are shown in Table 6.

TABLE 6

| | Example 1 dosed with Formulation 1 | Example 1 dosed with Formulation 2 | Example 1 dosed with Formulation 3 | Example 1 dosed with Formulation 4 | Example 1 dosed with Formulation 5 |
|---|---|---|---|---|---|
| Dose (mg/kg) | 2.5 | 2.5 | 3.75 | 3.75 | 0.5 |

TABLE 6-continued

|  | Example 1 dosed with Formulation 1 | Example 1 dosed with Formulation 2 | Example 1 dosed with Formulation 3 | Example 1 dosed with Formulation 4 | Example 1 dosed with Formulation 5 |
|---|---|---|---|---|---|
| $T_{max}$ (hours) | 4 | 4 | 4 | 4 | 1 |
| $C_{max}$ (ng/mL) | 182 | 420 | 768 | 644 | 290 |
| AUC (ng-hr/mL) | 2141 | 3873 | 7519 | 6366 | 697 |
| CL (ml/hour) | 934 | 516 | 465 | 549 | 716 |
| $T_{1/2}$ (hours) | 5.3 | 5.3 | 6.6 | 6.1 | 0.94 |

The results indicate that the formulations of Example 1 according to the present invention as described herein provide for acceptable sustained release formulations with improved pharmacokinetic parameters and flatter release profiles which may result in attenuated side effects and improved efficacy. For instance, Formulation 1 is shown to have an approximately 24-hour release profile after a single subcutaneous injection, with significantly low $C_{max}$ and long $T_{max}$. Moreover, all of the pamoate salt formulations of Example 1, i.e., Formulations 1-4, are shown to have significantly increased $T_{1/2}$ compared to the acetate salt formulation of Example 1, i.e., Formulation 5, as shown in Table 6.

Additional embodiments of the present invention will be apparent from the foregoing disclosure and are intended to be encompassed by the invention as described fully herein and defined in the following claims.

What is claimed is:

1. A pharmaceutical composition for subcutaneous or intramuscular injection comprising a melanocortin receptor peptide ligand wherein
said peptide is a pamoate salt of Ac-Arg-cyclo(Cys-D-Ala-His-D-Phe-Arg-Trp-Cys)-NH2;
said peptide is dissolved in a Polyethylene Glycol (PEG) 200 or PEG400 aqueous solution in which the volume-to-volume ratio of PEG to water is from about 1:9 to about 1:1 and the weight-to-volume concentration of said peptide is between about 200 mg/mL and about 300 mg/mL; and
said composition is a solution, a gel, a semi-solid or a suspension.

2. The pharmaceutical composition according to claim 1, wherein the pH of said composition is between about 3.0 and about 8.0.

3. The pharmaceutical composition according to claim 2, wherein said pamoate salt of Ac-Arg-cyclo(Cys-D-Ala-His-D-Phe-Arg-Trp-Cys)-NH$_2$ is dissolved in a PEG400/aqueous solution, in which the volume-to-volume ratio of PEG400 to water is about 1:1 and the weight-to-volume concentration of the peptide is about 200 mg/mL.

4. The pharmaceutical composition according to claim 2, wherein said pamoate salt of Ac-Arg-cyclo(Cys-D-Ala-His-D-Phe-Arg-Trp-Cys)-NH$_2$ is dissolved in a PEG200/aqueous solution, in which the volume-to-volume ratio of PEG200 to water is about 1:1 and the weight-to-volume concentration of the peptide is about 200 mg/mL.

5. The pharmaceutical composition according to claim 2, wherein said pamoate salt of Ac-Arg-cyclo(Cys-D-Ala-His-D-Phe-Arg-Trp-Cys)-NH2 is dissolved in a PEG400/Phosphate Buffered Saline (PBS) solution, in which the volume-to-volume ratio of PEG400 to PBS is about 1:1 and the weight-to-volume concentration of the peptide is about 300 mg/mL.

6. The pharmaceutical composition according to claim 2, wherein said pamoate salt of Ac-Arg-cyclo(Cys-D-Ala-His-D-Phe-Arg-Trp-Cys)-NH$_2$ is dissolved in a PEG400/saline solution, in which the volume-to-volume ratio of PEG400 to saline solution is about 1:1 and the weight-to-volume concentration of the peptide is about 300 mg/mL.

7. The pharmaceutical composition according to claim 1, further comprising a preservative, m-cresol, phenol, benzyl alcohol, methyl paraben, an isotonic agent, a stabilizer, imidazole, arginine, histidine, a surfactant, a chelating agent, a buffer or a divalent metal ion, or any combination thereof.

8. The pharmaceutical composition according to claim 7, wherein said preservative or isotonic agent is present in a concentration from about 0.01 mg/mL to about 100 mg/mL.

9. The pharmaceutical composition according claim 7, wherein said buffer is selected from the group consisting of Tris, ammonium acetate, sodium acetate, glycine, aspartic acid, and Bis-Tris.

10. The pharmaceutical composition according to claim 7, wherein said divalent metal is zinc.

* * * * *